US008423153B2

(12) United States Patent
Tiedtke

(10) Patent No.: US 8,423,153 B2
(45) Date of Patent: Apr. 16, 2013

(54) METHOD FOR PRODUCING IMPLANT STRUCTURES FOR CONTACTING OR ELECTROSTIMULATION OF LIVING TISSUE CELLS OR NERVES

(75) Inventor: Hans-Jurgen Tiedtke, Bonn (DE)

(73) Assignee: IMI Intelligent Medical Implants, AG, Zug (CH)

( * ) Notice: Subject to any disclaimer, the term of this patent is extended or adjusted under 35 U.S.C. 154(b) by 1090 days.

(21) Appl. No.: 12/296,519

(22) PCT Filed: Jan. 26, 2007

(86) PCT No.: PCT/EP2007/000686
§ 371 (c)(1),
(2), (4) Date: Jan. 20, 2009

(87) PCT Pub. No.: WO2007/118527
PCT Pub. Date: Oct. 25, 2007

(65) Prior Publication Data
US 2009/0234425 A1    Sep. 17, 2009

(30) Foreign Application Priority Data

Apr. 13, 2006  (DE) .......................... 10 2006 017 549

(51) Int. Cl.
*A61N 1/04*        (2006.01)

(52) U.S. Cl.
USPC ............................................. 607/115; 607/2

(58) Field of Classification Search .................. 607/1, 2, 607/115
See application file for complete search history.

(56) References Cited

U.S. PATENT DOCUMENTS 4,969,468 A  *  11/1990  Byers et al. ................... 600/373
5,720,099 A      2/1998  Parker et al.
(Continued)

FOREIGN PATENT DOCUMENTS

DE        10360624        7/2005
DE        69637280        5/2008
(Continued)

OTHER PUBLICATIONS

PCT International Preliminary Report on Patentability relating to International Application No. PCT/EP2007/000686, date of issuance of this report Nov. 17, 2008 (1 pg.).

(Continued)

*Primary Examiner* — Joseph Dietrich
(74) *Attorney, Agent, or Firm* — Workman Nydegger

(57) ABSTRACT

The object, to create a method for producing multilayers or multilayer systems wherein the structures generated on a substrate can easily be jointly detached from the substrate and are preserved in a composite, is achieved by the present invention by means of a method for producing implant structures comprising generating a first metal layer on a substrate, generating a second metal layer above the first metal layer, producing a number of multilayered implant structures above the second metal layer, removing the first metal layer between the substrate and the second metal layer, and releasing the implant structures from the substrate in a coherent composite. With the method according to the invention, between the implant structures and the substrate a release layer is generated consisting of two or three metal layers which serve as sacrificial layer in the course of releasing the fully processed multilayers by means of an under-etching process. As a result, a uniform and reliable separation of the finished multilayers from the substrate in a composite is achieved, facilitating the subsequent technology for assembly and interconnection of the implant structures.

28 Claims, 3 Drawing Sheets

U.S. PATENT DOCUMENTS

Figure 1:
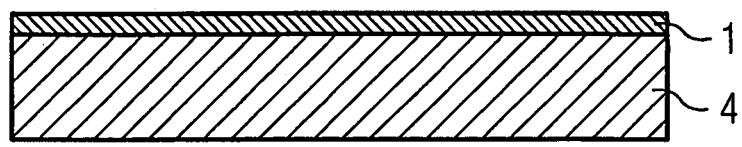

| | | | |
|---|---|---|---|
| 2002/0108781 A1* | 8/2002 | Mune et al. ................ | 174/264 |
| 2003/0195601 A1 | 10/2003 | Hung et al. | |
| 2005/0100828 A1 | 5/2005 | Kim et al. | |
| 2005/0164376 A1 | 7/2005 | Balagadde et al. | |
| 2005/0239272 A1 | 10/2005 | Ruttkowski et al. | |
| 2006/0053625 A1 | 3/2006 | Kim et al. | |

FOREIGN PATENT DOCUMENTS

| | | |
|---|---|---|
| EP | 1 096 026 A2 | 5/2001 |
| EP | 1 557 396 A2 | 7/2005 |
| JP | 2001252897 | 9/2001 |
| JP | 2004141978 | 5/2004 |
| WO | WO 01/04964 A1 | 1/2001 |
| WO | WO03/009432 | 1/2003 |
| WO | WO03/063692 | 8/2003 |
| WO | WO 2005/065432 A2 | 7/2005 |
| WO | WO2006/130558 | 12/2006 |

OTHER PUBLICATIONS

PCT English Translation of the Written Opinion of the International Searching Authority relating to International Application No. PCT/EP2007/000686 (7 pgs.).

International Search Report and Written Opinion for International Application No. PCT/EP2007/000686 mailed May 8, 2007; 9 pages.

Holmes, A.S., Saidam, S.M., Lawes, R.A., "Low Cost Liga Processes", The Institution of Electrical Engineers, 1997; 4 pages.

Banks, Danny, "General Introduction to Micromachining", The Institution of Electrical Engineers, 1997; 6 pages.

* cited by examiner

METHOD FOR PRODUCING IMPLANT STRUCTURES FOR CONTACTING OR ELECTROSTIMULATION OF LIVING TISSUE CELLS OR NERVES

This Application is the national stage of PCT/EP2007/000686 filed Jan. 26, 2007 which claims priority to German Application DE 10 2006 017 549.2 filed Apr. 13, 2006 published as Publication No. DE102006017549 on Oct. 18, 2007, the disclosures of which are hereby incorporated by reference in their entirety.

The present invention relates generally to implant structures and systems that serve for contacting living tissue or nerves. The invention relates in particular to a method for producing multilayered implant structures (multilayer-system implant structures, or multilayers) with at least one conductor-track plane having electrical conductor tracks for the electrical contacting of implants that serve for contacting or electrostimulation of living tissue cells or nerves.

Devices in the form of implants for stimulating living tissue, such as, for example, implants for the retina of the human eye or for the human inner ear, are known. As a rule, such implants include a number of stimulating electrodes, via which the electrical stimulating pulses are output to the surrounding tissue or to the cells, in order in this way to stimulate the nerves and hence to re-establish or improve the function thereof.

Known implants are frequently an integral part of systems that include electrical or electronic components for sensoric or diagnostic purposes, such as, for example, the electrical measurement of bodily functions, blood pressure, blood sugar or temperature. Stimulating systems may contain components for actoric purposes, such as, for example, for electrostimulation, defibrillation, emission of sound, or emission of ultrasound. As a rule, such systems include a substrate in the form of a printed circuit board, on which the electronic devices are arranged, with electrical contacts that are in direct or indirect contact with the body tissue, such as, for example, nerve tissue and muscle tissue, or with body fluids.

In order to keep the dimensions of the electrical or electronic components as small as possible, in addition to ceramic substrates flexible printed circuit boards made of plastics are also being increasingly employed. Such flexible printed circuit boards can be structured with the aid of established processes for producing microchips in very fine dimensions with a layer thickness of the conductor tracks up to a few hundred nanometres and with a thickness of the conductor track of, for example, a few micrometres.

Such a flexible printed circuit board consists, as a rule, of one or more insulating layers—for example, made of polyimide, parylenes, other plastics or insulators—on which conductor tracks, contact areas or, where appropriate, through-metallised holes are established between several conductor-track planes. For the electrical contacting of the conductor tracks, corresponding contact points are provided, via which, for example, external electrical lines and/or external devices can be connected, in order to connect the electronic components on the printed circuit board to external components of the stimulating system.

For the purpose of producing the flexible printed circuit boards, as a rule multilayer systems or so-called multilayers are generated which consist of several layers. These layers of the multilayer may include a number of conductor-track planes or conductor-track layers, in which electrically conducting conductor tracks are provided, and may also have a number of insulating layers which, for example, are arranged between two conductor-track layers, in order to insulate the latter from one another electrically.

Such multilayers frequently contain a relatively large number of individual structures which are simultaneously processed and built up on a common substrate. After the manufacturing procedure has been concluded, the multilayer has to be released from the substrate for further processing. Various techniques are described in the literature for releasing the processed multilayer systems from the substrate, wherein a release layer is applied and, after completion of the manufacturing process, is removed with a suitable means. The release layer may, for example, consist of photoresist, $SiO_2$, polymers, metals etc.

However, no technique is known in which the individual structures are preserved in the composite in the course of release from the substrate. In the known methods for production and release, the individual structures can only be released in separated form. However, the further processing of the separated structures is associated with a greater effort and hence also with higher costs than if the multilayers were still present in the composite also after their production.

It is therefore an object of the present invention to create a method for producing multilayers that enables an easy release from the substrate of the individual structures that have been generated. A further object of the present invention consists in creating a method in which the individual structures generated on a substrate can be jointly detached from the substrate and can thereby be preserved in the composite.

This object is achieved by the method according to the invention having the features according to claim 1. Advantageous further developments of the invention are specified in each of the dependent claims.

According to the present invention, the aforementioned object is achieved by a method for producing multilayered implant structures with at least one conductor-track plane with electrical conductor tracks for the electrical contacting of, for example, implants that, for example, serve for contacting or electrostimulation of living tissue cells or nerves, said method comprising the following steps:

generating a first metal layer on a substrate,
generating a second metal layer above the first metal layer,
producing a multilayer comprising a number of multilayered implant structures above the second metal layer,
removing the first metal layer between the substrate and the second metal layer, and
releasing the multilayered implant structures from the substrate in a coherent composite.

In this way, with the method according to the invention there is generated between the multilayer and the substrate a release layer consisting of two metal layers which serve as sacrificial layer in the course of releasing the fully processed multilayer by means of a wet-chemical under-etching process. As a result, a uniform and reliable separation of the finished multilayers from the substrate is achieved. Hence the method according to the invention has the advantage that all the individual-implant structures generated on the substrate are jointly released from the substrate in a composite and not individually. This facilitates the subsequent technology for assembly and interconnection with regard to automation and processing.

This advantageous effect of the method according to the invention is based on the fact that the release of the multilayers that have been generated is effected via a release layer made of metal, which consists of a first and a second metal layer which are removed together by one or more suitable etching processes when the multilayer has been fully processed. This release procedure is favoured by the selection of suitable metal layers, and, as a result, an easy release of the fully processed multilayers from the substrate is made possible. The substrate may consist of silicon, glass or ceramic, for example.

Whereas the first metal layer (sacrificial layer) is preferably manufactured from chromium, the material from which the second metal layer is generated is preferably so chosen that the material of the second metal layer brings about, by reason of its position in the electrochemical series of the elements in relation to the material of the first metal layer, a potential difference in relation to the first metal layer. As a result, an electrochemical voltage arises between the first metal layer (sacrificial layer) and the second metal layer, which favours the dissolution of the sacrificial layer in the course of the underetching process and hence the release of the implant structures from the substrate. By way of material for the second metal layer, use may be made of gold, silver, palladium or another noble metal, for example.

At high process temperatures, however, diffusion processes may occur between the first and second metal layers which hinder a release of the finished multilayers from the substrate by under-etching of the sacrificial layer. This is because at high temperatures the gold from the second metal layer can diffuse into the first metal layer, and/or the chromium from the first metal layer can diffuse into the second metal layer. As a result, an alloy that is no longer to be dissolved by an etching procedure is formed at the boundary between the first and second metal layers. It is therefore particularly advantageous if a third metal layer is inserted between the first and second metal layers, which thus serves as diffusion barrier between the first and second metal layers.

This diffusion barrier of the third metal layer arranged between the first and second metal layers prevents a diffusion of gold from the second metal layer into the first metal layer. By reason of the diffusion barrier, the multilayers can also be processed at temperatures above 250° C. The third metal layer performs its function as diffusion barrier between the first and the second metal layer particularly well if the third metal layer has been produced from titanium or tungsten titanium. The insertion of the third metal layer does not negatively influence the process of release of the first metal layer.

The removal of a metal layer in the method according to the invention is typically effected via an etching process. For an etching process, use is typically made of an etchant that is characteristic of the respective metal of the metal layer to be etched, and to this extent selective, with the aid of which typically only one metal layer can be (partially) removed in each instance. In the case of the etching of the sacrificial layer (metal layer 1), if this layer consists of chromium in the preferred embodiment, in particular an acidic aqueous solution of cerium ammonium nitrate is employed, with use typically being made of acetic acid for the purpose of acidification. The metal layer 3, if consisting of titanium, for example, is typically etched with strongly diluted hydrofluoric acid; if consisting of tungsten titanium, on the other hand, typically with hydrogen peroxide. The etching media that are selective for a particular metal in each instance are known to a person skilled in the art.

In a preferred embodiment, the multilayer, which comprises several implant structures, is surrounded by a rigid frame, for example in the form of a fixed ring, which is formed or applied around the implant structures of the multilayer, preferably on the outer edge of the multilayer. In this case the individual implant structures are connected to one another via thin webs in the course of being released from the substrate and are clamped in the stiff ring, enabling simple handling of the individual implant structures. This also facilitates the subsequent technology for assembly and interconnection in the course of further processing of the multilayers with regard to automation and processing. In the course of the further processing, the webs can then be separated, in order to obtain the fully composed individual structures.

In a preferred embodiment of the method according to the invention, in the course of the processing of the multilayer at least one electrically insulating material layer is generated, on which a conductor-track layer with at least one conductor track is arranged.

In another preferred embodiment of the present invention, the flexible printed circuit board for an implant consists of several layers of an insulating material with conductor tracks arranged between them or beneath them or above them.

A further object of the present invention consists in making available an intermediate product for producing implant structures, said intermediate product being distinguished by good handling qualities and simple further processing. This object is achieved by an intermediate product for producing implant structures that is composed of the following layers:
   a substrate,
   a first metal layer on the substrate,
   a second metal layer above the first metal layer and
   at least one multilayer with electrical conductor tracks for the electrical contacting of implants that serve for contacting or electrostimulation of living tissue cells or nerves.

Such an implant structure can be produced by the application of the first part of the aforementioned method according to the present invention or is obtainable in such a manner, whereby only the following method steps are implemented:
   generating a first metal layer on a substrate,
   generating a second metal layer above the first metal layer and
   producing a multilayer comprising a number of multilayered implant structures above the second metal layer.

Since in the case of this intermediate product the implant structures are still located on the stable substrate layer, the implant structures are well protected against mechanical loads. At this stage of the intermediate product the implant structures can therefore be transported safely for further processing at another place. The intermediate products for producing implant structures can be produced by the application of the aforementioned method according to the present invention, whereby only the following method steps are implemented:
   removing the first metal layer between the substrate and the second metal layer and
   releasing the multilayered implant structures from the substrate in a coherent composite.

As a result of the application of the second part of the aforementioned method according to the present invention on the intermediate product, the implant structures can be released from the substrate in a coherent composite and are consequently present in the same form as if the implant structures had been generated in one process after the complete method according to the invention with the first and second method parts.

According to a preferred embodiment, in the case of the implant structure according to the invention a third metal layer is provided on the first metal layer between the first metal layer and the second metal layer. In this case the first metal layer can be removed, in particular, by a wet-chemical underetching process, in order to act as sacrificial layer and, as a result, to detach the multilayer from the substrate.

Figure 2:
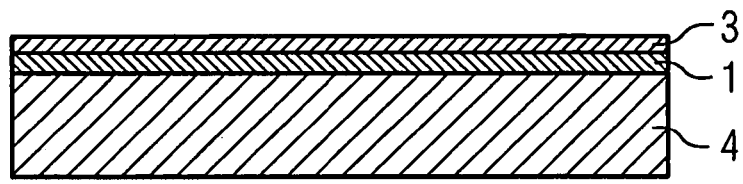
Figure 3:
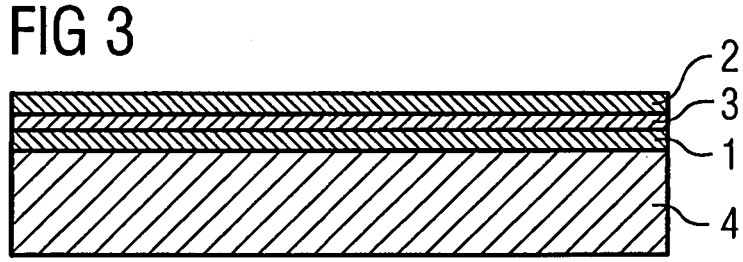
Figure 4:
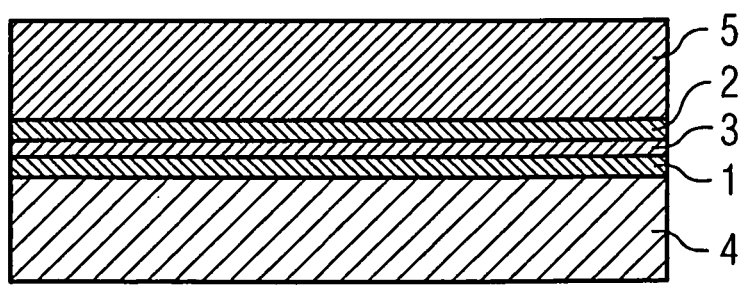
Figure 5:
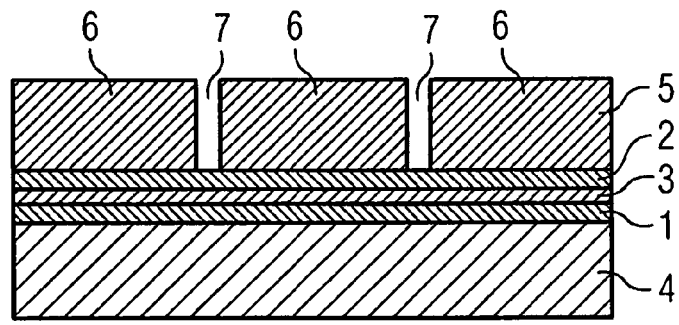
Figure 6:
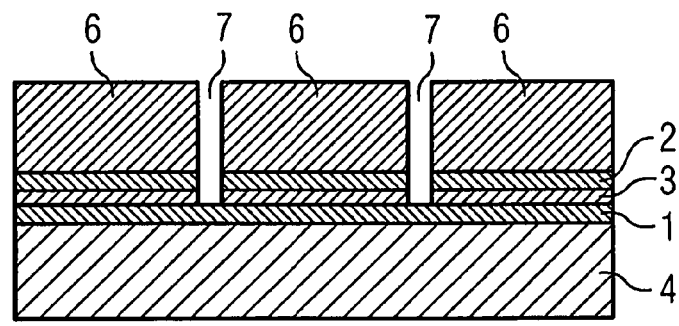
Figure 7:
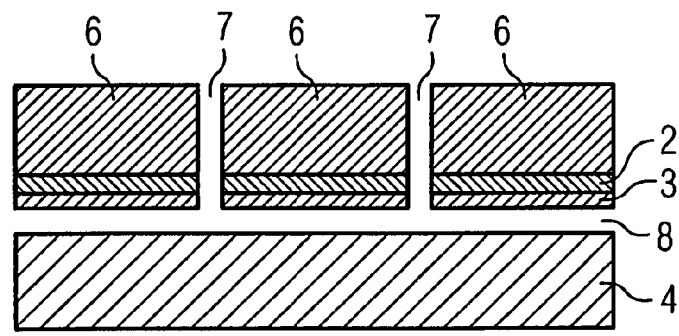
Figure 8:
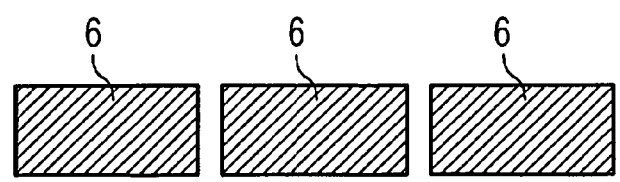
Figure 9:
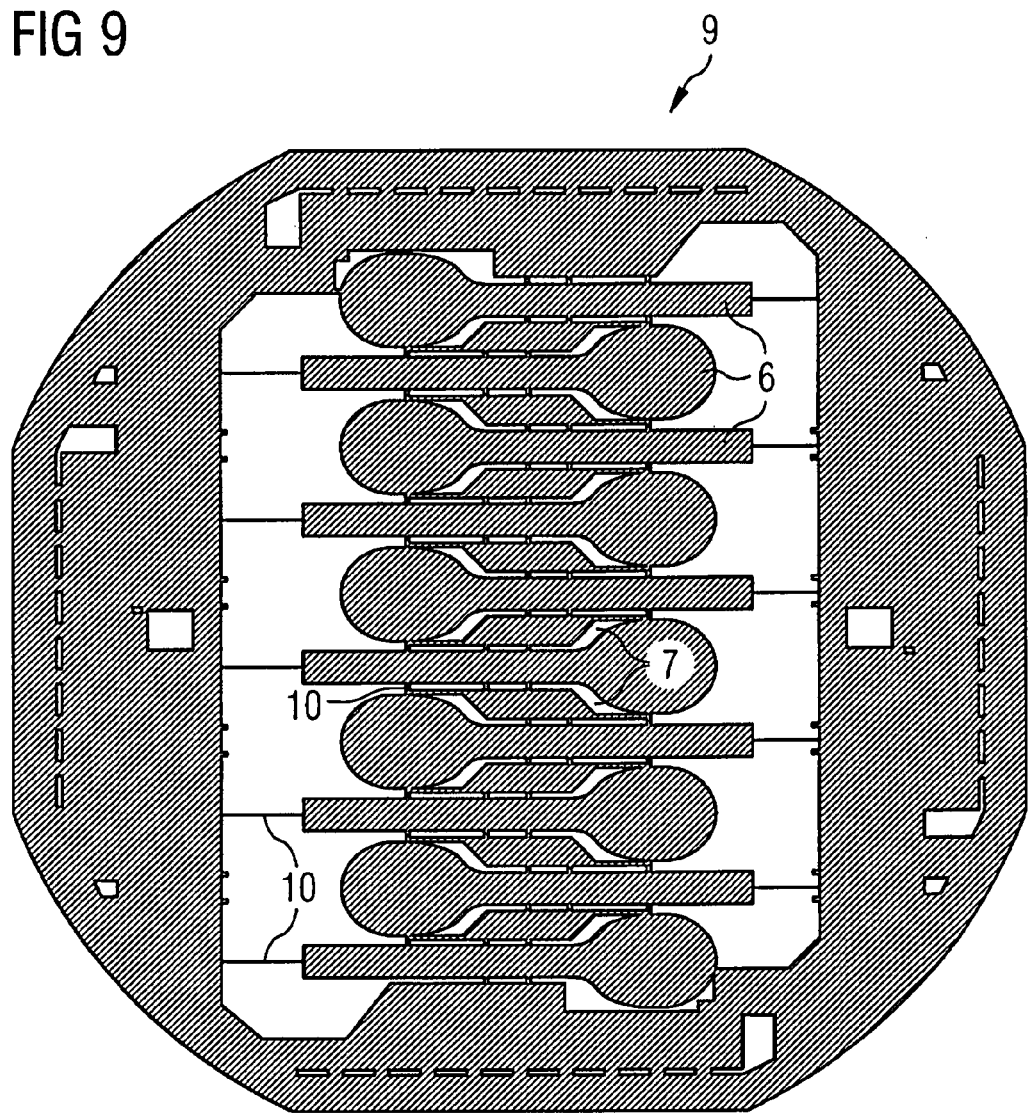

Further particulars, preferred embodiments and advantages of the present invention will become apparent from the following description with reference to the appended drawings. Shown are:

FIG. 1 a schematic representation of the configuration of an implant structure in the first step of a preferred embodiment of the method according to the present invention;

FIG. 2 a schematic representation of the configuration of an implant structure in the second step of a preferred embodiment of the method according to the present invention;

FIG. 3 a schematic representation of the configuration of an implant structure in the third step of a preferred embodiment of the method according to the present invention;

FIG. 4 a schematic representation of the configuration of an implant structure in the fourth step of a preferred embodiment of the method according to the present invention;

FIG. 5 a schematic representation of the configuration of an implant structure in the fifth step of a preferred embodiment of the method according to the present invention;

FIG. 6 a schematic representation of the configuration of an implant structure in the sixth step of a preferred embodiment of the method according to the present invention;

FIG. 7 a schematic representation of the configuration of an implant structure in the seventh step of a preferred embodiment of the method according to the present invention;

FIG. 8 a schematic representation of the configuration of an implant structure in the eighth step of a preferred embodiment of the method according to the present invention; and FIG. 9 a schematic representation from above of implant structures that have been produced in accordance with the method according to the invention and that have been released from the substrate in a composite.

The method according to the invention for producing and releasing implant structures in a composite will be described in the following. A schematic representation of the configuration of an implant structure in the first step of a preferred embodiment of the method according to the present invention is represented in FIG. 1. The method according to the invention builds upon a substrate 4 which, for example, consists of silicon, glass or ceramic. In the course of the first method step, firstly a first metal layer 1, which at a later time in the method serves as release layer or sacrificial layer, is applied on the substrate 4. This sacrificial layer 1 is produced, for example, from Cr or NiCr. The first metal layer 1 preferably has a thickness from 70 nm to 200 nm.

A schematic representation of the configuration of an implant structure in the second step of the method according to the invention is represented in FIG. 2 in a preferred embodiment. In the course of this second method step a third metal layer 3 is applied onto the first metal layer 1. This third metal layer 3 is produced, for example, from titanium or tungsten titanium, and serves later as diffusion barrier between the first metal layer 1 and the second metal layer 2. The third metal layer 3 preferably has a thickness from 50 nm to 200 nm.

A schematic representation of the configuration of an implant structure in the third step of the method according to the invention is represented in FIG. 3 in a preferred embodiment. In the course of this third method step a second metal layer 2 is applied onto the third metal layer 3, so that the third metal layer 3 is situated between the first metal layer 1 and the second metal layer 2. It has proved particularly advantageous if the second metal layer 2 is produced from gold. The second metal layer 2 preferably has a thickness from 50 nm to 300 nm. Generation of the metal layers 1, 2, 3 can be effected by suitable processes for depositing thin layers, such as, for example, by sputtering or other suitable processes.

A schematic representation of the configuration of an implant structure in the fourth step of the method according to the invention is represented in FIG. 4 in a preferred embodiment. In the course of this fourth method step, implant structures such as, for example, flexible multilayer systems or multilayers 5 with conductor-track planes and electrodes are processed on the second metal layer 2, the flexible layers of the multilayer 5 being produced from polyimide, for example. This fourth method step of the method according to the invention may also include several sub-processes, since in the course of these the actual implant structures 6 are generated. In this way, a multilayer 5 with several individual implant structures 6 is formed above the second metal layer 2. The processing and structuring of the multilayer 5 is effected, for example, with the aid of lithographic processes that are already established in microtechnology.

A schematic representation of the configuration of an implant structure in the fifth step of the method according to the invention is represented in FIG. 5 in a preferred embodiment. In the course of this fifth method step, the external geometry of the individual implant structures 6 is processed. By means of suitable structuring processes, vertical separating gaps 7 are generated between the individual implant structures 6, as far as the second metal layer 2. As a result, the implant structures or multilayers 6 are substantially separated from one another but are still connected to one another via thin webs 10 (see FIG. 9). These connecting webs 10 are preferably formed in the plane of the multilayers 6 and are constructed just like the multilayer 5.

A schematic representation of the configuration of an implant structure in the sixth step of the method according to the invention is represented in FIG. 6 in a preferred embodiment. In the course of this sixth method step, a wet-chemical etching of the two upper metal layers 2 and 3 is effected, i.e. at the exposed places the two upper metal layers 2 and 3 are removed, so that the vertical separating gaps 7 between the implant structures 6 extend as far as the first metal layer 1. The lowest metal layer or the first metal layer 1 (sacrificial layer) still remains.

A schematic representation of the configuration of an implant structure in the seventh step of the method according to the invention is represented in FIG. 7 in a preferred embodiment. In the course of this seventh method step, the sacrificial metal layer or first metal layer 1 is completely removed by a wet-chemical underetching, as a result of which a horizontal separating gap 8 is formed between the substrate 4 and the implant structures 6 in the composite. In this method step, the etching solution penetrates from above through the separating gaps 7 and begins to under-etch the implant structures 6 at the exposed places in the lateral direction, as a result of which a horizontal separating gap 8 is generated. By reason of the horizontal separating gap 8, the implant structures 6 have now been released from the substrate 4 completely and in a composite.

A schematic representation of the configuration of an implant structure in the eighth step of the method according to the invention is represented in FIG. 8 in a preferred embodiment. In the course of this eighth and last method step, the two metal layers 2 and 3 that have remained on the underside of the implant structures 6 are removed, for example by suitable etching processes, so that only the implant structures 6 are left behind.

A schematic representation from above of the implant structures 6 that have been produced by the method according to the invention and that have been released from the substrate in a composite is represented in FIG. 9. By virtue of the vertical separating gaps 7, the implant structures 6 are substantially separated from one another but are still connected to one another via thin webs 10. Consequently, with the method according to the invention the implant systems 6 can be released from the substrate 4 in a composite and processed further. This simplifies the handling of the thin flexible multilayers 6 and facilitates the subsequent technology for assembly and interconnection of the implant systems 6 with regard to automation and processing of the further treatment.

LIST OF REFERENCE SYMBOLS 1 first metal layer or sacrificial layer
2 second metal layer
3 third metal layer or diffusion barrier
4 substrate
5 multilayer
6 implant structures
7 vertical separating gaps between the implant structures 6
8 separating gap between the implant structures 6 and the substrate 4
9 composite of implant structures 6
10 webs between the implant structures 6

The invention claimed is:

1. A method for producing multilayered implant structures with at least one conductor-track plane having electrical conductor tracks for the electrical contacting of implants that serve for contacting or electrostimulation of living tissue cells or nerves, comprising the following steps:
generating a first metal layer on a substrate,
generating a second metal layer above the first metal layer,
producing a multilayer comprising a number of multilayered implant structures above the second metal layer,
removing the first metal layer between the substrate and the second metal layer, and thereby
releasing the multilayered implant structures from the substrate in an interconnected composite.

2. The method according to claim 1, wherein, between the generating of the first metal layer and the generating of the second metal layer, a third metal layer is generated on the first metal layer, so that the third metal layer is formed between the first metal layer and the second metal layer and serves as a diffusion barrier between the first and second metal layers.

3. The method according to claim 1, wherein the first metal layer serves as a sacrificial layer which is removed after the production of the implant structures, thereby to separate the produced implant structures from the substrate.

4. The method according to claim 1, wherein the removal of the first metal layer between the substrate and the second metal layer is effected by a wet-chemical under-etching process.

5. The method according to claim 1, wherein, after the production of the implant structures, the first metal layer is removed by a wet-chemical under-etching process, whereby the implant structures generated on the substrate are released from the substrate.

6. The method according to claim 2, wherein, after the production of the multilayer between the individual implant structures, at least one separating gap is generated which substantially separates the implant structures from one another.

7. The method according to claim 6, wherein the separating gaps between the implant structures of the multilayer extend in the vertical direction as far as the second metal layer.

8. The method according to claim 6, wherein the implant structures are substantially separated from one another by the separating gaps and are connected to one another via thin connecting webs.

9. The method according to claim 8, wherein the connecting webs are generated together with the implant structures of the multilayer.

10. The method according to claim 1, wherein a rigid frame which at least partially surrounds the implant structures of the multilayer is formed or arranged around the multilayer.

11. The method according to claim 6, wherein, after the generation of the separating gaps, the second and third metal layers are removed at the exposed places by one or more wet-chemical etching processes, so that the separating gaps extend between the implant structures as far as the first metal layer.

12. The method according to claim 11, wherein, after the removal of the second and third metal layers in the region of the separating gaps, the first metal layer is removed, whereby the implant structures generated on the substrate are released from the substrate.

13. The method according to claim 12, wherein, after the removal of the first metal layer, the remaining metal layers on the underside of the implant structures are removed by at least one etching process.

14. The method according to claim 1, wherein the first metal layer is manufactured from chromium or NiCr.

15. The method according to claim 1, wherein the first metal layer is generated with a layer thickness from about 70 nm to 200 nm.

16. The method according to claim 1, wherein the second metal layer is generated from a material that, by reason of its position in the electrochemical series of the elements in relation to the material of the first metal layer, brings about a difference between the first and the second metal layers, so that an electrochemical voltage arises between the first metal layer and the second metal layer.

17. The method according to claim 1, wherein the second metal layer is produced from gold.

18. The method according to claim 1, wherein the second metal layer is generated with a layer thickness from 50 nm to 200 nm.

19. The method according to claim 2, wherein the third metal layer is produced from titanium or from tungsten titanium.

20. The method according to claim 2, wherein the third metal layer is generated with a layer thickness from 50 nm to 200 nm.

21. The method according to claim 2, wherein the generation of the metal layers is effected by processes for depositing thin layers or by sputtering.

22. The method according to claim 1, wherein the production of implant structures includes a number of processes for building up and/or structuring the implant structures, whereby the multilayer is formed above the second metal layer.

23. The method according to claim 22, wherein a structuring of the implant structures is effected by means of lithographic processes.

24. The method according to claim 1, wherein in the course of producing the implant structures at least one electrically insulating material layer is generated, on which a conductor-track layer with at least one conductor track is arranged.

25. An intermediate product for producing an implant structure at least comprising the following layers:
a substrate,
a first metal layer on the substrate,
a second metal layer above the first metal layer, and
at least one multilayer above the second metal layer, wherein the multilayer comprises a plurality of interconnected multilayered implant structures with electrical conductor tracks for the electrical contacting or electrostimulation of living tissue cells or nerves.

26. The Intermediate product for producing an implant structure according to claim 25 obtained by means of the following steps:
generating a first metal layer on a substrate,
generating a second metal layer above the first metal layer and
producing a multilayer comprising a number of multilayered implant structures above the second metal layer.

27. The Intermediate product for producing an implant structure according to claim 25, wherein between the first metal layer and the second metal layer a third metal layer is provided on the first metal layer.

28. The Intermediate product for producing an implant structure according to claim 25, wherein the first metal layer is removable, by a wet-chemical under-etching, thereby resulting in the detachment of the multilayer from the substrate.

* * * * *